US009889166B2

(12) United States Patent
Mogna

(10) Patent No.: US 9,889,166 B2
(45) Date of Patent: Feb. 13, 2018

(54) TREATING LOW PRODUCTION OF MUCUS IN THE GASTROINTESTINAL TRACT WITH S. THERMOPHILUS

(71) Applicant: PROBIOTICAL S.P.A., Novara (IT)

(72) Inventor: Giovanni Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 14/417,768

(22) PCT Filed: Jul. 30, 2013

(86) PCT No.: PCT/IB2013/001668
§ 371 (c)(1),
(2) Date: Jan. 27, 2015

(87) PCT Pub. No.: WO2014/020408
PCT Pub. Date: Feb. 6, 2014

(65) Prior Publication Data
US 2015/0202239 A1 Jul. 23, 2015

(30) Foreign Application Priority Data

Jul. 30, 2013 (IT) .............................. MI2012A1328

(51) Int. Cl.
| | |
|---|---|
| A61K 36/03 | (2006.01) |
| A61K 35/747 | (2015.01) |
| A61K 36/886 | (2006.01) |
| A61K 35/744 | (2015.01) |
| A61K 47/36 | (2006.01) |
| A61K 47/42 | (2017.01) |
| A61K 9/20 | (2006.01) |
| A23L 29/20 | (2016.01) |
| A23L 29/238 | (2016.01) |
| A23L 29/256 | (2016.01) |
| A23L 29/281 | (2016.01) |
| A23L 33/135 | (2016.01) |
| A61K 35/00 | (2006.01) |

(52) U.S. Cl.
CPC ............ *A61K 35/747* (2013.01); *A23L 29/20* (2016.08); *A23L 29/238* (2016.08); *A23L 29/256* (2016.08); *A23L 29/284* (2016.08); *A23L 33/135* (2016.08); *A61K 9/205* (2013.01); *A61K 35/744* (2013.01); *A61K 36/886* (2013.01); *A61K 47/36* (2013.01); *A61K 47/42* (2013.01); *A23V 2002/00* (2013.01); *A61K 2035/115* (2013.01); *A61K 2300/00* (2013.01)

(58) Field of Classification Search
None
See application file for complete search history.

(56) References Cited

U.S. PATENT DOCUMENTS

2009/0087418 A1  4/2009 Strozzi et al.

FOREIGN PATENT DOCUMENTS

| CN | 101611738 | | 12/2009 |
|---|---|---|---|
| CN | 101773221 | | 7/2010 |
| CN | 102283334 | | 12/2011 |
| EP | 2526939 | * | 11/2012 |
| EP | 2526939 A1 | | 11/2012 |
| ES | 2350436 | | 1/2011 |
| JP | 2002204669 | | 7/2002 |
| RU | 2410423 C2 | | 1/2011 |
| WO | WO2005/060937 | * | 7/2005 |
| WO | 2007140613 | | 12/2007 |
| WO | 2011018547 | | 2/2011 |
| WO | 2011122934 | | 10/2011 |
| WO | 2013034974 | | 3/2013 |
| WO | 2014020408 A1 | | 2/2014 |

OTHER PUBLICATIONS

Khalil, R., Pol J Microbiol. 2009;58(1):49-55.*
Zeng et al., Aliment Pharmacol Ther vol. 28, pp. 994-1002, 2008.*
De Vuyst et al., FEMS Microbiol Rev. Apr. 1999;23(2):153-77.*
Singh, et al, "Synbiotic (probiotic and ginger extract) loaded floating beads: A novel therapeutic option in an experimental paradigm of gastric ulcer" Journal of Pharmacy and Pharmacology, vol. 64, No. 2, Nov. 28, 2011, pp. 207-217.
Patel, et al., "Potential of Exopolysaccharides from Lactic Acid Bacteria", Indian J Microbiol (Jan.-Mar. 2012) 52 (1):3-12.
Yang. "Antimicrobial Compounds and Extracellular Polysaccharides Produced by Lactic Acid Bacteria: Structures and Properties", Academic Dissertation, to be presented, with the permission of the Faculty of Agriculture and Forestry of the University of Helsinki, for public criticism in Auditorium XII of the University Main Building, Alekasenterinkatu 5, on Mar. 24, 2000, Department of Food Technology, University of Helsiny, Helsinki 2000.
International Search Report dated Dec. 2, 2013 for PCT/IB2013/001668 filed on Jul. 30, 2013 in the name of Probiotical S.P.A.
Iwai, H. et al. "Microscopic Colitis with Granuloma which Responded to Steroid Therapy" *Internal Medicine* 2007 DOI: 10.2169/internalmedicine.46.0160, pp. 1551-1555.
Russian Office Action and Search Report issued for Russian Application No. 2015104728/15(007399), filed on behalf of Probiotical S.P.A. on May 11, 2015, dated Mar. 23, 2017. 15 pages (English Translation + Russian Original).

(Continued)

*Primary Examiner* — Irene Marx
(74) *Attorney, Agent, or Firm* — Steinfl + Bruno LLP

(57) ABSTRACT

A composition for a medical device is described. The composition comprises a specific mucoadherent gelling complex composed of EPS, exopolysaccharides of bacterial origin produced in situ in the gastrointestinal tract by specific selected bacterial strains, in association with vegetable gums and/or animal and/or vegetable gelatines. The complex is capable of establishing a complete barrier effect of a mechanical type extending throughout the whole gastrointestinal tract and can be used as a medication for the prevention and treatment of all pathologies connected to a deficiency in the barrier effect in the gastrointestinal area due to a low production of mucus, such as, by way of non-exhaustive example, intestinal permeability and bacterial translocation.

11 Claims, No Drawings

(56) References Cited

OTHER PUBLICATIONS

Guzganu. "Severe Diarrhea in a 4-Month-Old Baby Girl with Acute Gastroenteritis: A Case Report and Review of the Literature", Hindawi Publishing Corporation, *Case Reports in Gastrointestinal Medicine*, vol. 2012, Article ID 920375, Jan. 18, 2012. 5 pages.

Del Piano et al. "Assessment of the Capability of a Gelling Complex Made of Tara Gum and the Exopolysaccharides Produced by the Microorganism *Streptococcus thermophilus* ST10 to Prospectively Restore the Gut Physiological Barrier *A Pilot Study*", J Clin Gastroenterol vol. 48, Supp. 1, Nov./Dec. 2014. 6 pages.

Database WPI Week 20122, Dec. 21, 2011, Thomson Scientific, London, GB; AN 2012/A53874 XP002692370.

Database WPI Week 201010, Dec. 30, 2009, Thomson Scientific, London, GB; AN 2010-A78413 XP002692371.

Singh, et al, "Symbiotic (probiotic and ginger extract) loaded floating beads: A novel therapeutic option in an experimental paradigm of gastric ulcer" Journal of Pharmacy and Pharmacology, vol. 64, No. 2, Nov. 28, 2011, pp. 207-217.

Sohail, et al, "Survivability of probiotics encapsulated in alginate gell microbeads using a novel impinging aerosols method" International Journal of Food Microbiology, Elsevier Science Publishers, vol. 145, No. 1, Dec. 7, 2010, pp. 162-168.

Lin, et al., "Exopolysaccharides production as affected by acid bacteria and fermentation time", Food Chemistry 100 (2007) 1419-1423.

Patel, et al., "Potential of Exopolysaccharides from Lactic Acid Bacteria", Indian J Microbiol (Jan-Mar 2012) 52 (1):3-12.

Yang "Antimicrobial Compounds and Extracellular Polysaccharides Produced by Lactic Acid Bacteria: Structures and Properties", Academic Dissertation, to be presented, with the permission of the Faculty of Agriculture and Forestry of the University of Helsinki, for public criticism in Auditorium XII of the University Main Building, Alekasenterinkatu 5, on Mar. 24, 2000, Department of Food Technology, University of Helsiny, Helsinki 2000.

European Patent Office Communication pursuant to Rule 114(2) EPC dated May 12, 2015 for Application No. 13777111.9-1456 on behalf of Probiotical S.p.A.

Written Opinion for PCT/IB2013/001668 filed on Jul. 30, 2013 in the name of Probiotical S.P.A. dated Dec. 2, 2013.

\* cited by examiner

TREATING LOW PRODUCTION OF MUCUS IN THE GASTROINTESTINAL TRACT WITH S. THERMOPHILUS

CROSS REFERENCE TO RELATED APPLICATIONS

The present application is the US national stage of International Patent Application PCT/IT2013/001668 filed on Jul. 30, 2013 which, in turn, claims priority to Italian Patent Application MI2012A001328 filed on Jul. 30, 2012.

The present invention relates to a composition for a medical device comprising a specific mucoadherent gelling complex composed of EPS, exopolysaccharides of bacterial origin produced in situ in the gastrointestinal tract by specific selected bacterial strains, in association with vegetable gums and/or animal and/or vegetable gelatines. Said complex is capable of establishing a complete barrier effect of a mechanical type extending throughout the whole gastrointestinal tract and can be used as a medication for the prevention and treatment of all pathologies connected to a deficiency in the barrier effect in the gastrointestinal area due to a low production of mucus, such as, by way of non-exhaustive example, intestinal permeability and bacterial translocation.

It is known that bacteria in general, such as, for example, bacteria belonging to the species *Streptococcus thermophilus*, are sensitive to gastric juices and arrive in the gastrointestinal tract in reduced concentrations and with little vitality.

Furthermore, it is known that pathogenic bacteria attack and penetrate the intestinal mucosa more easily when the intestinal mucosa is inflamed or when little mucus is present on the intestinal wall.

There thus remains a need to be able to preserve, in sufficient number and in a good state of vitality, bacterial strains, such as, for example, bacteria belonging to the species *Streptococcus thermophilus*, which are already present in the bacterial flora of the intestine or are carried in the intestine. Moreover, there remains a need to preserve the intestinal mucosa in such a way as to avoid, reduce or at least oppose the action of pathogenic bacteria.

The subject matter of the present invention relates to a composition for a medical device having features as defined in the appended independent claim.

Preferred embodiments of the present invention will appear more clearly from the detailed description that follows and are claimed in the appended claims.

The Applicant has found it useful to develop a composition or a medical device (composition for a medical device) comprising or, alternatively, consisting of gums of bacterial origin, in particular exopolysaccharides (EPS), in association with vegetable gums and/or animal and/or vegetable gelatines, said gums of bacterial origin being produced by said bacteria in situ in the gastrointestinal tract in the presence of said vegetable gums and/or animal and/or vegetable gelatines. Said bacterial gum produced directly by the probiotic bacterial strains of the present invention together with the vegetable gums and/or the animal and/or vegetable gelatines, are capable of preserving and protecting the intestinal mucosa in such a way as to avoid, reduce or at least oppose the action of pathogenic bacteria which are deleterious for the mucosa itself.

In particular, the present invention relates to a composition or a medical device (composition for a medical device) comprising or, alternatively, consisting of gums of bacterial origin, in particular exopolysaccharides, produced by said bacteria in situ in the gastrointestinal tract in association with vegetable gums and/or animal and/or vegetable gelatines.

The Applicant has found a way to form a specific mucoadherent gelling complex, which is composed of EPS, exopolysaccharides of bacterial origin produced in situ in the gastrointestinal tract by specific selected bacterial strains, in association with vegetable gums and/or animal and/or vegetable gelatines.

The subject matter of the present invention relates to a specific mucoadherent gelling complex composed of EPS, exopolysaccharides of bacterial origin produced in situ in the gastrointestinal tract by specific selected bacterial strains, in association with vegetable gums and/or animal and/or vegetable gelatines, for use as a medication for the prevention and treatment of all pathologies connected to a deficiency in the barrier effect in the gastrointestinal area due to a low production of mucus, preferably in the case of intestinal permeability and bacterial translocation, as claimed in the appended claims.

For the sake of brevity, in the context of the present invention a composition or a medical device (composition for a medical device) will be referred to in general, in the remainder of the description, as "the compositions of the present invention".

The compositions of the present invention comprise or, alternatively, consist of at least one probiotic bacterial strain which is a producer of exopolysaccharides (abbreviated EPS) in association with a vegetable gum and/or an animal and/or vegetable gelatine.

Said at least one strain of EPS-producing strains is selected from the group comprising the bacterial strains belonging to the genera *Streptococcus*, *Lactobacillus* and *Bifidobacteria*. Said at least one bacterial strain is selected preferably from the group comprising or, alternatively, consisting of probiotic bacterial strains belonging to the species *Streptococcus thermophilus*, *Lactobacillus plantarum*, *Lactobacillus rhamnosus*, *Lactobacillus pentosus*, *Lactobacillus acidophilus*, *Lactobacillus brevis*, *Lactobacillus reuteri*, *Bifidobacterium breve*, *Bifidobacterium bifidum*, *Bidifobacterium lactis*, *Lactobacillus fermentum* and *Lactobacillus delbrueeckii*.

Said at least one bacterial strain is selected from the group comprising or, alternatively, consisting of probiotic bacterial strains belonging to the species *Streptococcus thermophilus*, *Lactobacillus plantarum* or *Lactobacillus rhamnosus*. Said probiotic bacterial strains must be EPS producers in situ in the gastrointestinal tract.

Advantageously, said EPS-producing bacterial strains belong to the species *Streptococcus thermophilus*.

The compositions of the present invention comprise or, alternatively, consist of one or two or three or four EPS-producing probiotic bacterial strains, selected from among the ones described, in association with a vegetable gum and/or an animal and/or vegetable gelatine.

The compositions of the present invention comprise or, alternatively, consist of one or two or three or four EPS-producing probiotic bacterial strains, selected from the group comprising or, alternatively, consisting of probiotic bacterial strains belonging to the species *Streptococcus thermophilus*, *Lactobacillus plantarum* or *Lactobacillus rhamnosus* in association with a vegetable gum and/or an animal and/or vegetable gelatine.

Advantageously, said one or two or three or four EPS-producing bacterial strains belong to the species *Streptococcus thermophilus*.

Embodiments comprising mixtures of two or three or four bacterial strains selected from among probiotic bacterial strains belonging to the species *Streptococcus thermophilus* and/or *Lactobacillus plantarum* and/or *Lactobacillus rhamnosus* in association with a vegetable gum and/or an animal and/or vegetable gelatine are also part of the present invention.

A gum is a dehydrated or lyophilized or dried material in the form of a powder or flakes which on coming into contact with water produces a gum gel in water (aqueous gel) or a gum gelatine. Alternatively, an already prepared gel or gelatine can be validly used.

The gums used are all gums for oral use which are allowed and used in food supplements and medical devices. In one embodiment, the vegetable gum and/or the animal and/or vegetable gelatine is selected from the group comprising or, alternatively, consisting of *Aloe, Aloe vera* (*Aloe vera—Aloe barbadensis* Miller, is a plant of the Aloaceae family), *Aloe arborescens*, alginates, xyloglucans (or xylogels), tannates, gelatine tannate, carrageenans, pectins, agar-agar and tara gum.

Advantageously, the vegetable gum and/or the animal and/or vegetable gelatine is selected from the group comprising or, alternatively, consisting of *Aloe arborescens*, gelatine tannate and tara gum.

In one embodiment, use is made of gelatine tannate (a complex of gelatine and tannic acid), which acts by mechanical means to protect inflamed intestinal mucosae. Gelatine tannate forms a mucoadhesive protective film of protein origin which protects the intestinal mucosa. However, from the time it is ingested to the time it arrives at its destination in the intestine, a vegetable gum and/or an animal or vegetable gelatine undergoes a slow but inexorable degradation as it passes from the stomach to the intestine. The gum degrades and loses its effectiveness in restoring the physiological functions of the intestinal walls.

This degradation is due to multiple factors, such as, for example pH, enzymes, attacks from endogenous bacterial flora, the effect of the gastroduodenal barrier and a dilution effect. Practically speaking, there is a loss of effectiveness that occurs progressively as the gelatine tannate passes through the gastrointestinal tract, also as the result of an attack by acid, bile salts, pancreatic juices and enzymes. When the gelatine tannate arrives in the colon it is in part degraded and thus less effective in protecting the walls of the intestine against pathogenic bacteria, which are able to penetrate it by means of their flagella.

The Applicant has found that gum of bacterial origin, produced in situ by the strains of the present invention selected from the group comprising or, alternatively, consisting of probiotic bacterial strains belonging to the species *Streptococcus thermophilus, Lactobacillus plantarum* or *Lactobacillus rhamnosus*, on the one hand, and a vegetable gum and/or an animal and/or vegetable gelatine, on the other hand, each have an effect of their own and they are complementary to each other.

The first effect is a gelling effect exerted by the vegetable gum and/or the animal and/or vegetable gelatine, and which is maximum in the stomach (maximum protection) and minimum in the colon due to the degradation and consequent loss of effectiveness in protecting inflamed intestinal mucosae.

The second effect is a protective effect exerted by the gum of bacterial origin, in particular by exopolysaccharides (EPS) produced in situ by the strains of the present invention selected from the group comprising or, alternatively, consisting of probiotic bacterial strains belonging to the species *Streptococcus thermophilus, Lactobacillus plantarum* or *Lactobacillus rhamnosus*. This second effect is minimum in the stomach and maximum in the colon, where the bacteria of the present invention, having arrived alive and vital and at a high concentration, produce EPS in situ.

Added together, these two mutually complementary effects ensure total coverage against bacterial infections in the stomach (due to the vegetable gum and/or the animal and/or vegetable gelatine) and in the gastrointestinal tract (due to the gum of bacterial origin).

The subject matter of the present invention relates to a composition or a medical device (composition for a medical device) for use as a medication for the prevention and the treatment of all pathologies connected to a deficiency in the barrier effect in the gastrointestinal area due to a low production of mucus.

The compositions of the present invention are capable of restoring the barrier effect that was lost because of insufficient protection of the mucosa in the gastrointestinal tract.

The compositions of the present invention are capable of preventing and treating infections, inflammations and disorders of the gastrointestinal tract, pathogenic bacteria, candidiasis and intestinal permeability.

The composition of the present invention is capable of forming a specific mucoadherent gelling complex, composed of EPS, exopolysaccharides of bacterial origin (produced by selected strains as specified below, belonging in particular to the species *Streptococcus thermophilus*, e.g. *Streptococcus thermophilus* ST10-DSM 25246, *Streptococcus thermophilus* (YO4) DSM 16592 or mixtures thereof in a ratio by weight comprised from 1:2 to 2:1, preferably 1:1, and tara gum, a polysaccharide of vegetable origin. Said gelling complex is capable of establishing a barrier effect of a mechanical type extending throughout the whole gastrointestinal tract.

Thanks to the presence of the gellant tara gum, the composition of the present invention is capable of forming a hydrogel within few minutes after ingestion, by virtue of its thixotropic characteristics, and of thereby creating, in the first part of the gastrointestinal tract, a barrier effect of a mechanical type against pathogenic bacteria and metabolites with pro-inflammatory action. This barrier effect is completed and extended for the entire length of the gastrointestinal tract by the presence of exopolysaccharides (EPS), produced in situ by probiotic bacterial strains belonging to the species *Streptococcus thermophilus*, as specified below, e.g. *Streptococcus thermophilus* ST10, *Streptococcus thermophilus* YO04 or mixtures thereof, which serve to increase the viscosity of the surrounding environment through an exclusively mechanical, self-regulated mechanism. The intake of the aforesaid bacteria conveys into the human intestine a source of molecules with a gelling activity, thus exerting an action which is totally complementary to that of tara gum. The above-mentioned mucoadherent gelling complex has an innovative property to be taken into consideration: during its intestinal transit, tara gum (like all gums of vegetable origin) is progressively degraded by the resident microbiota, so that its mechanically opposing gelling power is progressively reduced. The gradual decrease in the action of the vegetable gum is effectively compensated for by the gradual increase in the release, in the intestinal lumen, of exopolysaccharides (EPS), for example by the bacterial strain ST10 and/or YO04, which manifests its particular characteristics above all in the ileum and in the colon. As a result, the synergetic combination of tara gum and exopolysaccharides (EPS) ensures the presence of gelling molecules for the entire length of the gastrointestinal tract, thus maximizing and optimizing the mechanical barrier action of the product. The presence, production and retention of the hydrophilic gel in the lumen of the organ can therefore for the first time be considered really complete, with a first area in which the action of the vegetable gum is maximum and a second area in which the action of the exopolysaccharides (EPS) is maximum.

In one embodiment, the bacterial strains are selected from the group comprising or, alternatively, consisting of:

Streptococcus thermophilus DSM 16590 (YO2), deposited with the depositary institution DSMZ in Germany on 20 Jul. 2004, Streptococcus thermophilus DSM 16592 (YO4), deposited with the depositary institution DSMZ in Germany on 20 Jul. 2004, Streptococcus thermophilus DSM 17843 (YO8), deposited with the depositary institution DSMZ in Germany on 21 Jan. 2005, Streptococcus thermophilus DSM 25246 (ST10), deposited with the depositary institution DSMZ in Germany on 19 Sep. 2011, Streptococcus thermophilus DSM 25247 (ST11), deposited with the depositary institution DSMZ in Germany on 19 Sep. 2011, Streptococcus thermophilus DSM 25282 (ST12), deposited with the depositary institution DSMZ in Germany on 19 Sep. 2011.

The bacterial strains were deposited in accordance with the Budapest Treaty and are available to the public.

In one embodiment, the composition of the present invention comprises or, alternatively, consists of at least one bacterial strain selected from the group comprising or, alternatively, consisting of: Streptococcus thermophilus DSM 16590 (YO2), Streptococcus thermophilus DSM 16592 (YO4), Streptococcus thermophilus DSM 17843 (YO8) and Streptococcus thermophilus DSM 25246 (ST10) in association with a vegetable gum and/or an animal and/or vegetable gelatine selected from the group comprising or, alternatively, consisting of Aloe arborescens, gelatine tannate and tara gum.

In another embodiment, the composition of the present invention comprises or, alternatively consists of: Streptococcus thermophilus DSM 25246 (ST10) in association with a vegetable gum and/or an animal and/or vegetable gelatine selected from the group comprising or, alternatively, consisting of Aloe arborescens, gelatine tannate and tara gum; advantageously tara gum.

In another embodiment, the composition of the present invention comprises or, alternatively, consists of: Streptococcus thermophilus DSM 25246 (ST10) and at least one strain selected from among Streptococcus thermophilus DSM 16590 (YO2), Streptococcus thermophilus DSM 16592 (YO4) and Streptococcus thermophilus DSM 17843 (YO8) in association with a vegetable gum and/or an animal and/or vegetable gelatine selected from the group comprising or, alternatively, consisting of Aloe arborescens, gelatine tannate and tara gum; advantageously tara gum.

In another embodiment, the composition of the present invention comprises or, alternatively, consists of: Streptococcus thermophilus DSM 25246 (ST10) and Streptococcus thermophilus DSM 16592 (YO4) in association with a vegetable gum and/or an animal and/or vegetable gelatine selected from the group comprising or, alternatively, consisting of Aloe arborescens, gelatine tannate and tara gum; advantageously tara gum. In the case of probiotic bacteria belonging to the species Streptococcus thermophilus, said bacteria are in a protected form (coated bacteria). The bacteria can be coated with one lipid coating (mono-coated) or two lipid coatings (bi-coated) of animal or vegetable origin (microencapsulated form). The lipid coating has a melting point comprised from 35 to 85° C., preferably from 45 to 75° C., even more preferably from 55 to 65° C. Alternatively, the bacteria can be inserted into a capsule, preferably made of soft or hard gelatine. The capsule can be coated with a gastroprotective film that is able to pass beyond the gastric barrier.

The bacterial strains specified above are present in the composition of the present invention in an amount comprised from 0.1 to 50% by weight, preferably from 0.5 to 15% by weight, even more preferably from 1 to 10%, relative to the total weight of the composition or supplement. However, said percentage depends on the pharmaceutical form it is desired to produce. For example, in the case of a capsule, the amount of said bacteria is greater than 30%, for example greater than 35%. In one embodiment, the composition comprises a mixture of bacterial strains at a concentration comprised from $1\times10^6$ to $1\times10^{11}$ CFU/g, preferably from $1\times10^8$ to $1\times10^{10}$ CFU/g of mixture or individual bacterial strain.

In one embodiment, the composition comprises bacterial strains at a concentration comprised from $1\times10^6$ to $1\times10^{11}$ CFU/dose, preferably from $1\times10^8$ to $1\times10^{10}$ CFU/dose. The dose can be comprised from 0.2 to 10 g, for example, it can be 0.25 g, 1 g, 3 g, 5 g or 7 g. The bacterial strains can be present in the composition in solid form, for example in the form of a powder, dehydrated powder or lyophilized powder.

EXPERIMENTAL PART

1. The viscosity of samples of serum fermented with probiotic bacterial strains belonging to the exopolysaccharide (EPS) producing species S. thermophilus was evaluated. The viscosity was measured by means of a viscometer which measures the rotation of a suitably sized disk within the sample to be tested: the more friction the disk encounters the slower its rotation, the set speed being equal. The result is expressed in centipoises (CPs), in association with a percentage SP, which is an expression of the goodness of the data (the method requires it to be greater than or equal to 15%). The culture medium is 10% reconstituted serum pasteurized at 80° C. for 20 minutes, into which the strains specified below were inoculated at a concentration of 3%: Streptococcus thermophilus DSM 16590 (YO2), Streptococcus thermophilus DSM 16592 (YO4), Streptococcus thermophilus DSM 17843 (YO8), Streptococcus thermophilus DSM 25246 (ST10), Streptococcus thermophilus DSM 25247 (ST11) and Streptococcus thermophilus DSM 25282 (ST12).

| | Viscosity | | | | PH | |
|---|---|---|---|---|---|---|
| | 5 hours | | 24 hours | | 5 hours | 24 hours |
| Sample | CPs | SP % | CPs | SP % | | |
| plain serum (blank 1) | 0-10 | 1.5-2 | 40 | 9 | 6.03 | 5.95 |
| serum + MO3 (bianco 2) | 10 | 3.5 | 70 | 15 | 4.55 | 4.17 |
| serum + YO2 -DSM 16590 | 40 | 9 | 170 | 35.5 | 4.67 | 4.14 |
| serum + YO4 -DSM 16592 | 40 | 8.5 | 210 | 43.5 | 4.63 | 4.10 |
| serum + YO8 -DSM 17843 | 20 | 5.5 | 120 | 25.5 | 4.68 | 4.09 |
| serum + ST10 -DSM 25246 | 40 | 9 | 210 | 42.5 | 4.57 | 4.05 |

-continued

| | Viscosity | | | | PH | |
| --- | --- | --- | --- | --- | --- | --- |
| | 5 hours | | 24 hours | | 5 hours | 24 hours |
| Sample | CPs | SP % | CPs | SP % | | |
| serum + ST11 -DSM 25247 | 10 | 3.5 | 70 | 15 | 4.63 | 4.1 |
| serum + ST12 -DSM 25282 | 60 | 13.5 | 90 | 18.5 | 4.62 | 4.1 |

2. Shown below are the analytic data found for a finished product in tablet form (tablets 1 to 8), based on identical mixtures which differed only in the gum used. Tara gum was used for tablets 1, 3, 5 and 7, whereas guar gum was used for tablets 2, 4, 6 and 8, the other ingredients and concentrations being equal.

The above-mentioned tablets were prepared in an identical manner, using the same ingredients and the bacterial strains specified below.

Tablet 1: strain ST10-DSM 25246, excipients and tara gum.
Tablet 2: strain ST10-DSM 25246, excipients and guar gum.
Tablet 3: strain ST10-DSM 25246 and strain YO4-DSM 16592, excipients and tara gum.
Tablet 4: strain ST10-DSM 25246 and strain YO4-DSM 16592, excipients and guar gum.
Tablet 5: strain ST10-DSM 25246 and strain YO2-DSM 16590, excipients and tara gum.
Tablet 6: strain ST10-DSM 25246 and strain YO2-DSM 16590, excipients and guar gum.
Tablet 7: strain ST10-DSM 25246 and strain YO8-DSM 17843, excipients and tara gum.
Tablet 8: strain ST10-DSM 25246 and strain YO8-DSM 17843, excipients and guar gum.

Compression tests were performed on the mixtures and the bacterial count was subsequently determined to evaluate the stress and mortality caused when forming the tablets.

| Tablet | Compression force | Hardness | CFU/g |
| --- | --- | --- | --- |
| 1 (tara gum) | 26 KN | 6-7 kp | $1.6 \times 10^9$ |
| | 22 KN | 4-6 kp | $1.9 \times 10^9$ |
| 2 (guar gum) | 22 KN | 7-8 kp | $0.9 \times 10^9$ |
| 3 (tara gum) | 26 KN | 6-7 kp | $1.7 \times 10^9$ |
| | 22 KN | 4-6 kp | $2.0 \times 10^9$ |
| 4 (guar gum) | 22 KN | 7-8 kp | $1.1 \times 10^9$ |
| 5 (tara gum) | 26 KN | 6-7 kp | $1.7 \times 10^9$ |
| | 22 KN | 4-6 kp | $2.1 \times 10^9$ |
| 6 (guar gum) | 22 KN | 7-8 kp | $1.0 \times 10^9$ |
| 7 (tara gum) | 26 KN | 6-7 kp | $1.6 \times 10^9$ |
| | 22 KN | 4-6 kp | $1.9 \times 10^9$ |
| 8 (guar gum) | 22 KN | 7-8 kp | $0.9 \times 10^9$ |

As can be observed, a higher count is obtained with tara gum than with guar gum under the same compression force of 22 KN; even when the compression force on the tara gum mixture is increased to 26 KN, the count obtained is nonetheless higher than the one obtained for the same mixture with guar gum.

The invention claimed is:

1. A method for treating a pathology in a subject having a low production of mucus in the gastrointestinal mucosal barrier, the method comprising:
   administering to the subject an effective amount of a mucoadherent gelling complex composed of viable exopolysaccharides-producing bacterial strains in combination with a vegetable gum, and/or an animal gelatin and/or a vegetable gelatin, the exopolysaccharides-producing bacterial strains capable of in situ production of exopolysaccharides in the gastrointestinal tract of the subject,
   wherein said pathology is selected from infections of pathogenic bacteria, inflammations and disorders of the gastrointestinal tract and candidiasis, and
   wherein said exopolysaccharides-producing bacterial strains comprise at least one Streptococcus thermophilus strain selected from the group consisting of:
   Streptococcus thermophilus DSM 16590 (YO2), deposited with the depositary institution DSMZ in Germany on 20 Jul. 2004,
   Streptococcus thermophilus DSM 16592 (YO4), deposited with the depositary institution DSMZ in Germany on 20 Jul. 2004,
   Streptococcus thermophilus DSM 17843 (YO8), deposited with the depositary institution DSMZ in Germany on 21 Dec. 2005,
   Streptococcus thermophilus DSM 25246 (ST10), deposited with the depositary institution DSMZ in Germany on 19 Sep. 2011,
   Streptococcus thermophilus DSM 25247 (ST11), deposited with the depositary institution DSMZ in Germany on 19 Sep. 2011, and
   Streptococcus thermophilus DSM 25282 (ST12), deposited with the depositary institution DSMZ in Germany on 19 Sep. 2011.

2. The method according to claim 1, wherein the low production of mucus occurs in the case of intestinal permeability and of a bacterial translocation.

3. The method according to claim 1, wherein said exopolysaccharide-producing bacterial strains further comprise bacterial strains of viable Lactobacillus plantarum and/or Lactobacillus rhamnosus capable of producing exopolysaccharides in situ in the gastrointestinal tract to protect the intestinal mucosa from the action of pathogenic bacteria.

4. The method according to claim 1, wherein the vegetable gum and/or vegetable gelatin is Aloe vera or Aloe arborescens.

5. The method according to claim 1, wherein the vegetable gum and/or vegetable gelatin is an alginate or tara gum.

6. The method according to claim 1, wherein the vegetable gum and/or vegetable gelatin is a xyloglucan or xylogel.

7. The method according to claim 1, wherein the at least one Streptococcus thermophilus strain is selected from the group consisting of Streptococcus thermophilus DSM 16590 (YO2), Streptococcus thermophilus DSM 16592 (YO4), Streptococcus thermophilus DSM 17843 (YO8) and Streptococcus thermophilus DSM 25246 (ST10), and
   the vegetable gum and/or the animal and/or vegetable gelatine is selected from the group consisting of Aloe arborescens, gelatine tannate and tara gum.

8. The method according to claim 7, wherein said composition mucoadherent gelling complex comprises:
   Streptococcus thermophilus DSM 25246 (ST10) in combination with a vegetable gum and/or a vegetable gelatin selected from the group consisting of Aloe arborescens and tara gum.

9. The method according to claim 7, wherein said mucoadherent gelling complex comprises:
   Streptococcus thermophilus DSM 25246 (ST10) and at least one strain selected from the group consisting of

*Streptococcus thermophilus* DSM 16590 (YO2), *Streptococcus thermophilus* DSM 16592 (YO4) and *Streptococcus thermophilus* DSM 17843 (YO8) in combination with a vegetable gum and/or a vegetable gelatin selected from the group consisting of *Aloe arborescens* and tara gum.

10. The method according to claim 7, wherein said mucoadherent gelling complex comprises:

*Streptococcus thermophilus* DSM 25246 (ST10) and *Streptococcus thermophilus* DSM 16592 (YO4) in combination with a vegetable gum and/or a vegetable gelatin selected from the group consisting of *Aloe arborescens* and tara gum.

11. The method according to claim 8, wherein the vegetable gum and/or the vegetable gelatin is tara gum.

* * * * *